US010238661B2

(12) United States Patent
Huband

(10) Patent No.: US 10,238,661 B2
(45) Date of Patent: Mar. 26, 2019

(54) FUSED, SPIROCYCLIC HETEROAROMATIC COMPOUNDS FOR THE TREATMENT OF BACTERIAL INFECTIONS

(71) Applicant: Entasis Therapeutics Limited, London (GB)

(72) Inventor: Michael Huband, Waltham, MA (US)

(73) Assignee: Entasis Therapeutics Limited, London (GB)

( * ) Notice: Subject to any disclaimer, the term of this patent is extended or adjusted under 35 U.S.C. 154(b) by 94 days.

(21) Appl. No.: 15/314,660

(22) PCT Filed: May 27, 2015

(86) PCT No.: PCT/IB2015/001585

§ 371 (c)(1),
(2) Date: Nov. 29, 2016

(87) PCT Pub. No.: WO2015/181637

PCT Pub. Date: Dec. 3, 2015

(65) Prior Publication Data

US 2018/0169104 A1 Jun. 21, 2018

Related U.S. Application Data

(60) Provisional application No. 62/004,246, filed on May 29, 2014.

(51) Int. Cl.
*A61K 31/42* (2006.01)
*A61K 31/527* (2006.01)
*A61K 31/538* (2006.01)

(52) U.S. Cl.
CPC ............ *A61K 31/527* (2013.01); *A61K 31/42* (2013.01); *A61K 31/538* (2013.01)

(58) Field of Classification Search
USPC ...................................................... 514/235.5
See application file for complete search history.

(56) References Cited

U.S. PATENT DOCUMENTS

| | | | |
|---|---|---|---|
| 7,371,757 | B2 | 5/2008 | Morningstar et al. |
| 8,039,466 | B2 | 10/2011 | Hubschwerlen et al. |
| 8,658,641 | B2 | 2/2014 | Barvian et al. |
| 8,889,671 | B2 | 11/2014 | Basarab et al. |
| 9,040,528 | B2 | 5/2015 | Barvian et al. |
| 9,187,495 | B2 | 11/2015 | Basarab et al. |
| 9,540,394 | B2 | 1/2017 | Basarab et al. |
| 9,839,641 | B2 | 12/2017 | Basarab et al. |
| 2012/0157428 | A1 | 6/2012 | Albrecht et al. |
| 2014/0088093 | A1 | 3/2014 | Curtis et al. |
| 2015/0368266 | A1 | 12/2015 | Barvian et al. |

FOREIGN PATENT DOCUMENTS

| | | | |
|---|---|---|---|
| WO | 2004/031195 | A1 | 4/2004 |
| WO | 2006/120563 | A2 | 11/2006 |
| WO | 2007/072151 | A1 | 6/2007 |
| WO | 2009/04382 | A2 | 1/2009 |
| WO | 2010/043893 | A1 | 4/2010 |
| WO | 2014/114929 | A1 | 7/2014 |

OTHER PUBLICATIONS

Kohlhoff et al., “In vitro activity of AZD0914, a novel DNA gyrase inhibitor, against Chlamydia trachomatis and Chlamydia pneumoniae.,” Antimicrobial Agents and Chemotherapy 58(12): 7595-96 (2014).
Waites et al., “In vitro antibacterial activity of AZD0914 against human mycoplasmas and ureaplasmas,” Antimicrob Agents Chemother. 59(6): 3627-9 (2015).
Huband et al., “In vitro antibacterial activity of ADZ0914 and comparators against mycoplasma, ureaplasma, and chlamydia,” (Abstract Only) Retrieved from the internet: <icaaonline.com/php/icaac2014abstracts/data/papers/2014/F-265.htm> on Oct. 30, 2015.
Huband et al., “In vitro antibacterial activity of AZD0914: A new spiropyrimidinetrione bacterial DNA Gyranse inhibitor against potential agents of bioterrorism,” Retrieved from the internet: <icaaonline.com/php/icaac2014abstracts/data/papers/2014/F-264.htm> on Oct. 30, 2015.
U.S. Appl. No. 13/124,889, filed Jun. 8, 2011, U.S. Pat. No. 8,658,641 Feb. 25, 2014, Granted.
U.S. Appl. No. 14/153,320, filed Jan. 13, 2014, U.S. Pat. No. 9,040,528, May 26, 2015, Granted.
U.S. Appl. No. 14/159,773, filed Jan. 21, 2014, U.S. Pat. No. 8,889,671, Nov. 18, 2014, Granted.
U.S. Appl. No. 14/515,684, filed Oct. 16, 2014, U.S. Pat. No. 9,187,495, Nov. 17, 2015, Granted.
U.S. Appl. No. 14/881,595, filed Oct. 13, 2015, U.S. Pat. No. 9,540,394, Jan. 10, 2017, Granted.
U.S. Appl. No. 15/353,325, filed Nov. 16, 2016, U.S. Pat. No. 9,839,641, Dec. 12, 2017, Granted.
International Search Report for PCT/GB2009/051363; dated Feb. 26, 2010.
International Search Report for PCT/GB2014/050164; dated May 27, 2014.
Krasnov et al., “Diastereoselective Synthesis of 1-Alkyl-2,4,6-troxoperhydropyrimidine-5-spiro-3'-(1',2',3',4'-tetrahydroquinolines)”, Tetrahedron (2010), 66(32):6054-6061.
Miller et al., “Discovery and Characterization of QPT-1, the Progenitor of a New Class of Bacterial Topoisomerase Inhibitors”, Antimicrobial Agents & Chemotherapy (2008), 52(8)2806-2812.
Rabong et al., “Scope and Limitations of the T-Reaction Employing Some Functionalized C—H-Acids and Naturally Occurring Secondary Amines”, Heterocycles (2008); 75; 5; 799-838.
Ruble et al., “Synthesis of (−)-PNU-286607 by Asymmetric Cyclization of Alkylidene Barbituates”, JACS (2009), 131 (11)3991-3997.

*Primary Examiner* — Kathrien A Cruz
(74) *Attorney, Agent, or Firm* — McCarter & English, LLP; Steven G. Davis; Michael J DeGrazia

(57) ABSTRACT

Disclosed are methods for treating various bacterial infections with (2R,4S,4aS)-11-fluoro-2,4-dimethyl-8-[(4S)-4-methyl-2-oxo-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione, or a pharmaceutically acceptable salt thereof.

6 Claims, No Drawings

FUSED, SPIROCYCLIC HETEROAROMATIC COMPOUNDS FOR THE TREATMENT OF BACTERIAL INFECTIONS

CROSS REFERENCE TO RELATED APPLICATIONS

This application is a 35 U.S.C. § 371 national stage filing of International Application No. PCT/IB2015/001585, filed on May 27, 2015, which in turn claims the benefit of priority of U.S. Provisional Application No. 62/004,246, filed on May 29, 2014. The entire contents of each of the foregoing applications are incorporated herein by reference.

BACKGROUND

Antibiotic tolerance and resistance has become a grave threat to the successful treatment of many common bacterial infections. Indeed, according to the Infectious Disease Society of America, methicillin resistant *Staphylococcus aureus* (MRSA) kills more Americans every year than emphysema, HIV/AIDS, Parkinson's disease and homicide combined. Not only is multi-drug resistance in common infectious Gram-positive and -negative pathogens such as *Enterococcus faecium, Staphylococcus aureus, Klebsiella pneumoniae, Acinetobacter baumannii, Pseudomonas aeruginosa, Mycobacterium tuberculosis* and *Enterobacter* species on the rise, but evidence of resistance is being seen in *Salmonella* and *Clostridium difficile*, and increasingly *Neisseria gonorrhoeae* (Gerard D. Wright, "Antibiotics: A New Hope," 19 (2012), 3-10). Due to this increase in resistance, the development of new antibacterial medicines is an important medical need.

SUMMARY

There remains a need for new therapies for treating bacterial infections. There is provided the compound (2R,4S,4aS)-11-fluoro-2,4-dimethyl-8-[(4S)-4-methyl-2-oxo-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione, or a pharmaceutically acceptable salt thereof, for potential use for treating bacterial infections.

In one aspect, there is provided a method for treating a bacterial infection caused by *Bacillus anthracis, Bacillus cereus, Burkholderia* spp., *Brucella* spp., *Francisella* spp., *Yersina* spp., *Mycoplasma* spp., *Ureaplasma* spp., *Chlamydia trachomatis* or *Chlamydia pneumoniae* in a subject in need thereof comprising administering an effective amount of (2R,4S,4aS)-11-fluoro-2,4-dimethyl-8-[(4S)-4-methyl-2-oxo-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione, or a pharmaceutically acceptable salt thereof, to the subject.

In one aspect, there is provided the use of (2R,4S,4aS)-11-fluoro-2,4-dimethyl-8-[(4S)-4-methyl-2-oxo-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione, or a pharmaceutically acceptable salt thereof, for treating a bacterial infection caused by one or more bacterium selected from *Bacillus anthracis, Bacillus cereus, Burkholderia* spp., *Brucella* spp., *Francisella* spp., *Yersina* spp., *Mycoplasma* spp., *Ureaplasma* spp., *Chlamydia trachomatis* or *Chlamydia pneumoniae.*

In one aspect, there is provided the use of (2R,4S,4aS)-11-fluoro-2,4-dimethyl-8-[(4S)-4-methyl-2-oxo-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione, or a pharmaceutically acceptable salt thereof, in the manufacture of a medicament for treating a bacterial infection caused by one or more bacterium selected from *Bacillus anthracis, Bacillus cereus, Burkholderia* spp., *Brucella* spp., *Francisella* spp., *Yersina* spp., *Mycoplasma* spp., *Ureaplasma* spp., *Chlamydia trachomatis* or *Chlamydia pneumoniae.*

In one aspect, there is provided a pharmaceutical composition comprising (2R,4S,4aS)-11-fluoro-2,4-dimethyl-8-[(4S)-4-methyl-2-oxo-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione, or a pharmaceutically acceptable salt thereof, for treating a bacterial infection caused by one or more bacterium selected from *Bacillus anthracis, Bacillus cereus, Burkholderia* spp., *Brucella* spp., *Francisella* spp., *Yersina* spp., *Mycoplasma* spp., *Ureaplasma* spp., *Chlamydia trachomatis* or *Chlamydia pneumoniae.*

DETAILED DESCRIPTION

There are provided methods of treating bacterial infections caused by one or more bacterium selected from *Bacillus anthracis, Bacillus cereus, Burkholderia* spp., *Brucella* spp., *Francisella* spp., *Yersina* spp., *Mycoplasma* spp., *Ureaplasma* spp., *Chlamydia trachomatis* or *Chlamydia pneumoniae* by administering to a subject in need thereof an effective amount of (2R,4S,4aS)-11-fluoro-2,4-dimethyl-8-[(4S)-4-methyl-2-oxo-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione, or a pharmaceutically acceptable salt thereof.

The compound (2R,4S,4aS)-11-fluoro-2,4-dimethyl-8-[(4S)-4-methyl-2-oxo-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione has the following structure:

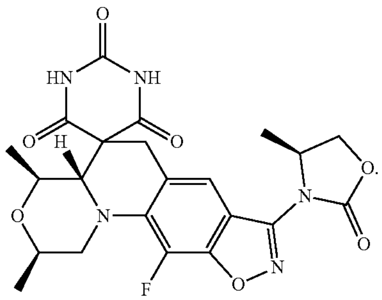 [SMILES: C[C@@H]1CN2c3c(cc4c(N5C(=O)OC[C@@H]5C)noc4c3F)CC3(C(=O)NC(=O)NC3=O)[C@H]2[C@H](C)O1]

The aforementioned compound, and its method of synthesis, is disclosed in International Application No. PCT/GB2014/050164, which is expressly incorporated herein in its entirety.

The language "bacterial infection" includes infections caused by one or more species of Gram-negative, Gram-positive, or atypical bacteria.

In some embodiments, the bacterial infection is caused by *Bacillus anthracis* or *Bacillus cereus.*

In some embodiments, the bacterial infection is caused by *Burkholderia* spp., for example, *Burkholderia mallei, Burkholderia pseudomallei* and *Burkholderia cepacia.*

In some embodiments, the bacterial infection is caused by *Brucella* spp., for example, *Brucella melitensis, Brucella abortus, Brucella canis, Brucella suis* and *Brucella ovis.*

In some embodiments, the bacterial infection is caused by *Francisella* spp., for example, *Francisella tularensis, Francisella novicida* and *Francisella philomiragia.*

In some embodiments, the bacterial infection is caused by *Yersina* spp., for example, *Yersinia pestis* and *Yersinia enterocolitica.*

In some embodiments, the bacterial infection is caused by *Mycoplasma* spp., for example *Mycoplasma gallisepticum, Mycoplasma genitalium, Mycoplasma haemofelis, Mycoplasma hominis, Mycoplasma hyopneumoniae, Mycoplasma ovipneumoniae* and *Mycoplasma pneumoniae.*

In some embodiments, the bacterial infection is caused by *Ureaplasma* spp., for example, *Ureaplasma parvum* and *Ureaplasma urealyticum*

In some embodiments, the bacterial infection is caused by *Chlamydia trachomatis* or *Chlamydia pneumoniae.*

In some embodiments, the bacteria are resistant to one or more antibacterials other than (2R,4S,4aS)-11-fluoro-2,4-dimethyl-8-[(4S)-4-methyl-2-oxo-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione. The language "resistance" and "antibacterial resistance" refers to bacteria that are able to survive exposure to one or more antibacterial agents. In one embodiment, the bacteria is resistant to one or more of an aminoglycoside antibiotic (e.g., amikacin, gentamicin, kanamycin, neomycin, netilmicin, tobramycin, paromomycin, spectinomycin), an ansamycin antibiotic (e.g., rifaximin, streptomycin), a carbapenem antibiotic (e.g., ertapenem, doripenem, imipenem/cilastatin, meropenem), a cephalosoprin antibiotic (e.g., cefadroxil, cefaxolin, cefatolin, cefalexin, cefaclor, cefamandole, cefoxitin, cefprozil, cefuroxime, cefisime, cefdinir, cefditoren, cefoperazone, cefotaxime, cefpodoxime, ceftazidime, certibuten, ceftizoxime, ceftriaxone, cefepime, ceftarolin fosamil, ceftobiprole), a glycopeptide antibiotic (e.g., teicoplanin, vancomycin, telavancin), a lincosamide anitbiotic (e.g., clindamycin, lincomycin), daptomycin, a macrolide antibiotic (e.g., azithromycin, clarithromycin, dirithromycin, erythromycin, roxithromycin, troleandomycin, telithromycin, spiramycin), aztreonam, furazolidone, nitrofuantoin, an oxazolidinone antibiotic (e.g., linezolid, posizolid, radezolid, torezolid), a penicillin antibiotic (e.g., amoxacillin, ampicillin, azlocillin, carbenicillin, cloxacillin, dicloxacillin, flucloxacillin, mezlocillin, methicillin, nafcillin, oxacillin, penicillin, piperacillin, temocillin, ticarcillin), amoxicillin/clavulante, ampicilin/sulbactam, piperacillin/tazobactam, ticarcillin/clavulanate, a quinolone antibacterial (e.g., ciprofloxacin, enoxacin, gatifloxacin, gemifloxacin, levofloxacin, lomefloxacin, moxifloxacin, nalidixic acid, norfloxacin, ofloxacin, trovafloxin, grepafloxacin, sparfloxacin, temafloxacin), a suflonamide antibiotic (e.g., mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim/sulfamethoxazole—TMP-SMX) and a tetracycline antibiotic (e.g., demeclocycline, doxycycline, minocycline, oxytetracycline, tetracycline, tigeclycline). In some embodiments, the bacteria is resistant to doxycycline. In some embodiments, the bacteria is resistant to levofloxacin and/or ciprofloxacin. In some embodiments, the bacteria is resistant to azithromycin. In some embodiments, the bacteria is resistant to tetracycline.

In some embodiments, there is provided a method of treating a subject suffering from a sexually transmitted bacterial infection comprising administering to the subject an effective amount of a (2R,4S,4aS)-11-fluoro-2,4-dimethyl-8-[(4S)-4-methyl-2-oxo-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione, or a pharmaceutically acceptable salt thereof.

In some embodiments, there is provided (2R,4S,4aS)-11-fluoro-2,4-dimethyl-8-[(4S)-4-methyl-2-oxo-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione, or a pharmaceutically acceptable salt thereof, for use in treating a bacterial infection caused by one or more bacterium selected from *Bacillus anthracis, Bacillus cereus, Burkholderia* spp., *Brucella* spp., *Francisella* spp., *Yersina* spp., *Mycoplasma* spp., *Ureaplasma* spp., *Chlamydia trachomatis* or *Chlamydia pneumoniae.*

In one aspect, there is provided a method for treating an anthrax infection, glanders, melioidosis, a pulmonary infection in a subject suffering from cystic fibrosis, brucellosis, tularemia, plague, sepsis, yersiniosis, pelvic inflammatory disease, atypical pneumonia, non-specific urethritis, pneumonia, bronchopulmonary dysplasia or meningitis in a subject in need thereof comprising administering an effective amount of (2R,4S,4aS)-11-fluoro-2,4-dimethyl-8-[(4S)-4-methyl-2-oxo-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione, or a pharmaceutically acceptable salt thereof, to the subject.

The language "treat," "treating" and "treatment" includes the reduction or inhibition of enzyme or protein activity related to a bacterial infection in a subject, amelioration of one or more symptoms of a bacterial infection in a subject, or the slowing or delaying of progression of a bacterial infection in a subject. The language "treat," "treating" and "treatment" also includes the reduction or inhibition of the bacterial growth, replication or a reduction or inhibition of the bacterial load of bacteria in a subject.

The term "subject" includes, for example, primates, cows, horses, pigs, sheep, dogs, cats, rabbits, rats, birds (including wild and domestic birds, such as turkeys, geese, chickens, ducks and the like) and mice. In some embodiments, the subject is a primate, for example, a human. In some embodiments, the subject is suffering from a Gram-positive bacterial infection. In some embodiments, the subject is suffering from a Gram-negative bacterial infection. In some embodiments, the subject is suffering from an atypical bacterial infection. In some embodiments, the subject is in need of treatment (e.g., the subject would benefit biologically or medically from treatment). In some embodiments, the subject is suffering from a significant underlying disease state that complicates the response to treatment of a bacterial infection, for example cystic fibrosis. In some embodiments, the subject is suffering from one or more bacterial infections (e.g., co-infected by two or more bacterial infections). In some embodiments, the subject is suffering from an infection caused by *Neisseria gonorrhoeae.* In some embodiments, the subject is co-infected with *Chlamydia trachomatis* and *Neisseria gonorrhoeae*. In some embodiments, the subject is at risk of contracting a sexually transmitted bacterial infection (e.g., a *Chlamydia trachomatis* or *Neisseria gonorrhoeae* infection).

The language "effective amount" includes an amount of (2R,4S,4aS)-11-fluoro-2,4-dimethyl-8-[(4S)-4-methyl-2-oxo-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione, or a pharmaceutically acceptable salt thereof, that will elicit a biological or medical response of a subject, for example, the reduction or inhibition of enzyme or protein activity related to a bacterial DNA gyrase or a bacterial infection, amelioration of symptoms of a bacterial infection, or the slowing or delaying of progression of a bacterial infection. In some embodiments, the language "effective amount" includes the amount of (2R, 4S,4aS)-11-fluoro-2,4-dimethyl-8-[(4S)-4-methyl-2-oxo-1, 3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione, or a pharmaceutically acceptable salt thereof, that when administered to a subject, is effective to at least partially alleviate, inhibit, and/or ameliorate a bacterial infection or inhibit bacterial DNA gyrase, and/or reduce or inhibit the bacterial growth, replication or bacterial load of a bacteria in a subject.

EXEMPLIFICATION

Example 1. Synthesis of (2R,4S,4aS)-11-fluoro-2,4-dimethyl-8-[(4S)-4-methyl-2-oxo-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione (Compound 1)

Compound 1 was synthesized as described below:

Intermediate 1

3-Chloro-6-[(2R,6S)-2,6-dimethylmorpholin-4-yl]-7-fluoro-1,2-benzoxazole-5-carbaldehyde

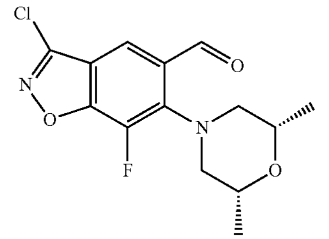 [SMILES: C[C@@H]1CN(c2c(C=O)cc3c(Cl)noc3c2F)C[C@H](C)O1]

To an ice cooled solution of 3-chloro-6,7-difluoro-1,2-benzoxazole-5-carbaldehyde (prepared according to the procedure described in International Application Publication No. WO 2010/043893, 5.0 g, 23.0 mmol) in anhydrous acetonitrile (50 ml) was added diisopropylethylamine (5.9 g, 45.9 mmol) followed by cis-2,6-dimethylmorpholine (2.6 g, 23.0 mmol) and the mixture was heated at 85° C. for 12 hours in a sealed tube. The solution was cooled to room temperature and the volatiles were removed under vacuum. The residue qwas dissolved in Ethyl acetate, washed with water followed by brine and then dried over anhydrous $Na_2SO_4$. Removal of solvent under vacuum afforded the crude product, which was purified over silica gel column using a gradient of ethyl acetate in pet. ether to give title compound as solid. Yield: 6.0 g (84%). $^1$H NMR (400 MHz, DMSO-$d_6$) δ: 1.0 (d, 6H), 2.9 (t, 2H), 3.1 (d, 2H), 3.8 (m, 2H), 7.7 (s, 1H), 10.2 (s, 1H). MS (ES) $MH^+$: 313 for $C_{14}H_{14}ClFN_2O_3$.

Intermediate 2

3-Chloro-6-[(2R,6S)-2,6-dimethylmorpholin-4-yl]-5-(1,3-dioxolan-2-yl)-7-fluoro-1,2-benzoxazole

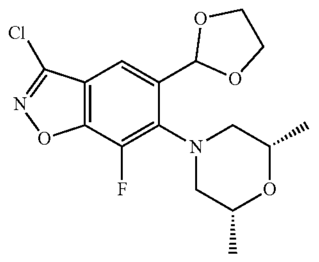 [SMILES: C[C@@H]1CN(c2c(C3OCCO3)cc3c(Cl)noc3c2F)C[C@H](C)O1]

A solution of Intermediate 1 (16.3 g, 52.2 mmol), ethylene glycol (8.1 g, 130.6 mmol) and pyridinium p-toluenesulfonate (1.31 g, 5.2 mmol) in toluene (300 mL) was heated at reflux in a Dean-Stark apparatus for 16 hours. The solvents were removed under vacuum and the residue was dissolved in diethyl ether (75 mL), washed with water (3×25 mL) and aqueous brine (25 mL). The organic layers were dried over anhydrous $Na_2SO_4$ and filtered. Removal of solvents under vacuum afforded the title compound, which was further purified by trituration with hot hexane. Yield: 18.0 g (80%). $^1$H NMR (400 MHz, DMSO-$d_6$) δ: 1.1 (d, 6H), 2.8 (t, 2H), 3.0 (d, 2H), 3.3 (m, 4H), 3.8 (m, 2H), 5.7 (s, 1H), 7.6 (s, 1H).

Intermediate 3

(4R)-3-{6-[(2R,6S)-2,6-Dimethylmorpholin-4-yl]-5-(1,3-dioxolan-2-yl)-7-fluoro-1,2-benzoxazol-3-yl}-4-methyl-1,3-oxazolidin-2-one

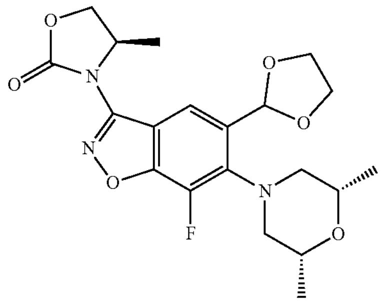 [SMILES: C[C@@H]1CN(c2c(C3OCCO3)cc3c(N4C(=O)OC[C@H]4C)noc3c2F)C[C@H](C)O1]

To a stirred solution of NaH (0.24 g, 9.9 mmol) in dimethylformamide (10 mL), a solution of (4R)-4-methyl-1,3-oxazolidin-2-one (synthesized according to the procedure described in Nishiyama, T.; Matsui, Shigeki; Yamada, F. *J. Het. Chem.* (1986), 23(5), 1427-9) (1.0 g, 9.9 mmol) in dimethylformamide (10 mL) was added slowly at 0° C. over a period of 10 minutes. The mixture was stirred at the room temperature for 30 minutes and a solution of Intermediate 2 (1.1 g, 3.1 mmol) in dimethylformamide (5 mL) was added at the same temperature. This mixture was heated at 80° C. for 12 hours and poured into ice-cooled water and extracted with ethyl acetate (2×20 mL). The organic layers were dried over anhydrous $Na_2SO_4$ and the solvents were removed under vacuum. The crude product was purified by silica gel column chromatography using a gradient of ethyl acetate in pet. ether. Yield: 0.15 g (12%). MS (ES) MH+: 422.4 for $C_{20}H_{24}FN_3O_6$.

Intermediate 4

(4S)-3-{6-[(2R,6S)-2,6-Dimethylmorpholin-4-yl]-5-(1,3-dioxolan-2-yl)-7-fluoro-1,2-benzoxazol-3-yl}-4-methyl-1,3-oxazolidin-2-one

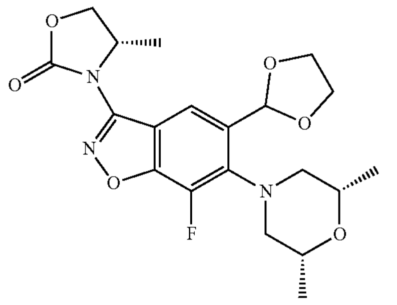 [SMILES: C[C@@H]1CN(c2c(C3OCCO3)cc3c(N4C(=O)OC[C@@H]4C)noc3c2F)C[C@H](C)O1]

Intermediate 4 was prepared from Intermediate 2 using (4S)-4-methyl-1,3-oxazolidin-2-one (synthesized according to the procedure described in Nishiyama, T.; Matsui, Shigeki; Yamada, F. *J. Het. Chem.* (1986), 23(5), 1427-9) in a method similar to the one described for the synthesis of Intermediate 3. MS (ES) MH+: 422.4 for $C_{20}H_{24}FN_3O_6$.

Compound 1

(2R,4S,4aS)-11-Fluoro-2,4-dimethyl-8-[(4S)-4-methyl-2-oxo-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

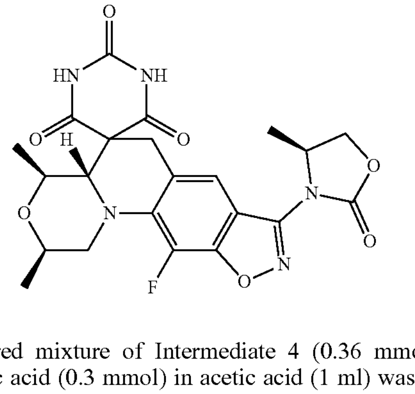

A stirred mixture of Intermediate 4 (0.36 mmol) and barbituric acid (0.3 mmol) in acetic acid (1 ml) was heated at 85° C. for 16 hours. The solvents were evaporated, the residue was dissolved in methanol (2 ml) and water (5 ml) was added. The precipitated solids were filtered and purified by reverse phase HPLC (10 mM ammonium acetate in water, $CH_3CN$), eluting two components. The second eluting component was isolated as a solid and identified as the title compound. The title compound was isolated by reverse phase HPLC (10 mM ammonium acetate in water, CH3CN) as the first eluting of two components. $^1H$ NMR (400 MHz, DMSO-$d_6$) δ: 0.9 (d, 3H), 1.15 (d, 3H), 1.4 (d, 3H), 2.9 (d, 1H), 3.1 (t, 1H), 3.5-3.6 (m, 2H), 3.8 (m, 1H), 3.9 (d, 1H), 4.0 (d, 1H), 4.2 (q, 1H), 4.6-4.7 (m, 2H), 7.6 (s, 1H), 11.5 (s, 1H), 11.8 (s, 1H). MS (ES) MH+: 488.4 for $C_{22}H_{22}FN_5O_7$; $[\alpha]_D^{20}$=−92 (c=1; MeOH).

Also isolated from the synthesis of Compound 1 as the second eluting component from HPLC purification was (2S,4R,4aR)-11-fluoro-2,4-dimethyl-8-[(4S)-4-methyl-2-oxo-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione

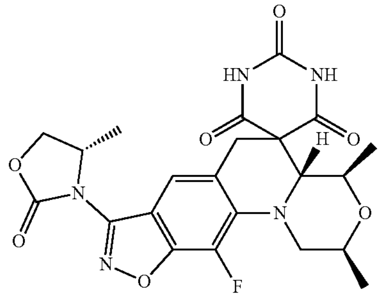 [SMILES: C[C@H]1CN2c3c(cc4c(N5C(=O)OC[C@@H]5C)noc4c3F)CC3(C(=O)NC(=O)NC3=O)[C@@H]2[C@@H](C)O1]

$^1H$ NMR (400 MHz, DMSO-$d_6$) δ: 0.9 (d, 3H), 1.15 (d, 3H), 1.4 (d, 3H), 2.9 (d, 1H), 3.1 (t, 1H), 3.6-3.7 (m, 2H), 3.8-4.0 (m, 1H), 3.9 (d, 1H), 4.1 (d, 1H), 4.2 (q, 1H), 4.6-4.7 (m, 2H), 7.6 (s, 1H), 11.5 (s, 1H), 11.8 (s, 1H). MS (ES) MH+: 488.4 for $C_{22}H_{22}FN_5O_7$; $[\alpha]_D^{20}$=+224 (c=1; MeOH).

Example 2. In Vitro Antibacterial Activity of Compound 1 Against Human Mycoplasmas Compound 1 is an investigational inhibitor of the supercoiling and decatenation activity of the DNA gyrase and topoisomerase IV with activities against several different types of bacteria. Preliminary data suggest this agent maintains activity against organisms that are resistant to other agents such as fluoroquinolones and tetracyclines, including agents of sexually transmitted infections such as *Neisseria gonorrhoeae*. The present study was undertaken to increase knowledge of the in vitro activities of Compound 1 against additional human pathogens by testing a small number of clinical isolates and reference strains representing five species of mollicutes that are important human pathogens. Organisms tested included *Mycoplasma pneumoniae, Mycoplasma hominis, Mycoplasma genitalium, Ureaplasma urealyticum* and *Ureaplasma parvum*. While *M. pneumoniae* is primarily a pathogen of the respiratory tract causing illnesses such as pharyngitis, tracheobronchitis, and pneumonia, the remaining species are important pathogens of the urogenital tracts in adult men and women and can also cause systemic disease in neonates when transmitted vertically during pregnancy or at delivery. Susceptibility testing was performed in accordance with guidelines of the Clinical Laboratory Standards Institute (CLSI) (CLSI 2011). Strains tested included organisms that contained the tetM gene, which mediates tetracycline resistance, mutations in 23S ribosomal RNA that confers macrolide resistance, and others that contained mutations in DNA gyrase and/or topoisomerase IV that confer resistance to fluoroquinolones.

Methods

Antibacterials.

Drugs included in the investigation are summarized in Table 1. An appropriate amount of each powdered drug was weighed to prepare 10 mL of a stock solution, allowing for the percentage purity of each. Antimicrobial agents were dissolved according to each manufacturer's instructions.

TABLE 1

| Test Compound and Control/Reference Compounds | | |
|---|---|---|
| Compound | Purity | Source |
| Compound 1 | 98.9% | |
| Azithromycin | 95.2% | Fluka/Sigma-Aldrich Switzerland |
| Doxycycline | 100% | Sigma-Aldrich St. Louis, MO |
| Levofloxacin | 99% | Sigma-Aldrich St. Louis, MO |

Bacterial Strains.

Pure cultures of clinical isolates of known titer derived from various body sites of adults and children that have been stored at minus 70° C. in the culture collections of the UAB Diagnostic *Mycoplasma* Laboratory were used in this investigation. Original sources of the isolates and year of isolation, when available, as well as specific resistance profiles, where relevant, are summarized in Table 2.

TABLE 2

Bacterial Strains Tested

| Accession No. or stock identifier | Year Isolated | Body Site Strain Designation | Comment |
|---|---|---|---|
| *Mycoplasma genitalium* (n - 5) | | | |
| M2341 | unknown | Urethra | Danish male with NGU |
| M30 | 1980 | Urethra ATCC 49895 | British male with NGU |
| M2321 | unknown | Urethra | Danish male with NGU |
| M6282 | unknown | Urethra | Japanese male with NGU |
| UTMB-10G | 1986 | Synovial fluid ATCC 49899 | Texas male with pneumonia and arthritis |
| G37 QC Strain ATCC 33530 | 1980 | Urethra | British male with NGU |
| *Mycoplasma pneumoniae* (n - 12) | | | |
| 54484 | 2009 | Throat | UAB Clinical isolate Macrolide-resistant |
| 54506 | 2009 | BAL | UAB Clinical isolate Macrolide-resistant |
| 55246 | 2010 | Throat | UAB Clinical isolate |
| 55612 | 2010 | Sputum | UAB Clinical isolate |
| 57807 | 2012 | BAL | UAB Clinical isolate |
| 58188 | 2012 | BAL | UAB Clinical isolate |
| 58772 | 2012 | BAL | UAB Clinical isolate |
| 59598 | 2013 | BAL | UAB Clinical isolate |
| 59597 | 2013 | BAL | UAB Clinical isolate |
| 53938 | 2009 | BAL | UAB Clinical isolate |
| 53706 | 2009 | BAL | UAB Clinical isolate |
| 51494 | 2006 | CSF | UAB Clinical isolate |
| M-129 QC Strain ATCC 29342-B7 | unknown | Respiratory tract | Patient with pneumonia |
| *Mycoplasma hominis* (n = 12) | | | |
| 10848 | 1991 | Endometrium | UAB Clinical isolate Contains tetM |
| 10505 | 1991 | Endometrium | UAB Clinical isolate Contains tetM |
| 59793 | 2013 | Cervix | UAB Clinical isolate |
| 59744 | 2013 | Cervix | UAB Clinical isolate |
| 58881 | 2012 | unknown | UAB Clinical isolate |
| 58603 | 2012 | Vagina | UAB Clinical isolate |
| 11124 | 1991 | Endometrium | UAB Clinical isolate |
| 11063 | 1991 | Endometrium | UAB Clinical isolate |
| 11140 | 1991 | Endometrium | UAB Clinical isolate Contains tetM gene |
| 11121 | 1991 | Endometrium | UAB Clinical isolate |
| 11612 | 1991 | Endometrium | UAB Clinical isolate |
| 12434 | 1992 | Endometrium | UAB Clinical isolate |
| PG21 QC Strain ATCC 23114 | unknown | Rectal swab | |

TABLE 2-continued

Bacterial Strains Tested

| Accession No. or stock identifier | Species | Year Isolated | Body Site | Comment |
|---|---|---|---|---|
| Ureaplasma species (n -15) | | | | |
| 25353 | Uu | 1997 | Pleural fluid | UAB Clinical isolate Contains tetM, Fluoroquinolone and-Macrolide-resistant |
| 48105 | Up | 2001 | Vagina | Fluoroquinolone-resistant |
| 48736 | Up | 2002 | unknown | UAB Clinical isolate |
| 51110 | Up | 2005 | unknown | UAB Clinical isolate Fluoroquinolone-resistant |
| 49718 | Uu | 2003 | unknown | UAB Clinical isolate Contains tetM |
| 50826 | Uu | 2005 | unknown | UAB Clinical isolate Contains tetM |
| 43306 | Uu | 1999 | Tissue | UAB Clinical isolate |
| 44062 | Uu | 1999 | Vagina | UAB Clinical isolate |
| 45623 | Up | 2000 | ETA | UAB Clinical isolate |
| 48750 | Up | 2002 | Rectal swab | UAB Clinical isolate |
| 52863 | Up | 2008 | ETA | UAB Clinical isolate |
| 59913 | Up/Uu | 2013 | Urethra | UAB Clinical isolate |
| 59967 | Up | 2013 | Urethra | UAB Clinical isolate |
| 60052 | Up/Uu | 2013 | Urethra | UAB Clinical isolate |
| 60153 | Up/Uu | 2013 | Vagina | UAB Clinical isolate Fluoroquinolone-resistant |
| Uu Serotype 9 QC Strain ATCC33175 | Uu | unknown | Urethra | Canadian male with NGU Contains tetM |

Notes for Table 2

Abbreviations: Uu = *Ureaplasma urealyticum*, Up = *Ureaplasma parvum*, BAL = bronchoalveolar lavage fluid, CSF = cerebrospinal fluid, ETA = endotracheal aspirate

*Ureaplasma* species were identified by real-time PCR as previously described (Xiao et al. Detection and characterization of human *Ureaplasma* species and serovars by real-time PCR. *J. Clin. Microbiol.* 2010, 48, 2715-2723). Three clinical isolates were shown to be a mixture of both species, which sometimes occurs (Xiao et al. Extensive horizontal gene transfer in ureaplasmas from humans questions the utility of serotyping for diagnostic purposes. *J. Clin. Microbiol.* 2011, 49, 2818-2826).

Presence of tetM in *M. hominis* and *Ureaplasma* species was determined by PCR in the UAB Diagnostic Mycoplasma Laboratory.

In Vitro Susceptibility Test Methods:

The assay employed for this investigation was the broth microdilution minimal inhibitory concentration (MIC) assay that was published in "Methods for Antimicrobial Susceptibility Testing of Human Mycoplasmas. Approved Guideline, CLSI Document M43-A" (CLSI 2011). This assay employs 96 well microtiter plates into which a defined inoculum of the organism to be tested is added to doubling dilutions of antimicrobial agents in small volumes. Plates were incubated until the growth control changed color. The MIC endpoint was then determined by lack of color change in broth containing a pH indicator. Specific aspects of the procedures that were used follow.

Media.

SP4 broth and SP4 agar were used for testing *M. pneumoniae* and *M. genitalium*. Modified Hayflick's *Mycoplasma* broth and agar were used for testing *M. hominis*. Shepard's 10B Broth and A8 agar were used for testing *Ureaplasma* species. These media and their formulations are described in the CLSI document (CLSI 2011).

Preparation of Inoculum.

Organisms were thawed to room temperature and diluted in appropriate prewarmed media in 50 mL conical tubes to yield a final inoculum of approximately $10^4$ CFU/mL. At least 5 mLs of inoculum was prepared for each drug, based on testing 8 dilutions in duplicate and appropriate controls. If more dilutions were needed to achieve endpoint MICs, an additional volume of inoculum was prepared. Inoculated broths were incubated aerobically at 37° C. for 2 hours prior to use to allow mycoplasmas to become metabolically active prior to inoculating microtiter plates. Due to their more rapid growth rates, ureaplasmas were incubated for only one hour prior to inoculating the plates.

Performance of Broth Microdilution Assay.

A single microtiter plate was used for 4 drugs. Each drug was tested in duplicate (Drug 1—rows A, B; Drug 2—rows C, D; Drug 3—rows E, F. Wells 9, 10, 11 and 12 were used for solvent, media, drug and growth controls, respectively. 0.025 mL of appropriate broth medium was added to rows 2-8 and 10 and 12 of the microtiter plate. 0.025 mL of the highest concentration of drug to be tested was added to wells 1, 2 and 11 in rows A, B. Well 11 served as the drug control. The other drugs to be tested were added the same way in their respective rows. The highest drug concentration was prepared by performing an appropriate dilution on the stock solution. Antimicrobial agents were serially diluted using a 0.025 mL multichannel pipette, beginning at the 2nd well, and continuing through well 8, discarding the final 0.025 mL. A solvent control was prepared in well 9 by incorporating 0.025 mL of the highest concentration (1:10 dilution in sterile deionized water) of solvent used to dissolve the antimicrobial agent being tested if any substance other than water was used as a solvent. 0.175 mL of the desired dilution of inoculated media that has been prewarmed for 2 hours was added to each well in rows 1-9 and 12. Well 12 served as the growth control. Inocula were added starting with well 12 and working backwards to well 1 to prevent drug carryover. 0.175 mL of appropriate uninoculated media was added to wells 10 and 11 (total of 0.2 mL) for media and drug controls. A final determination of the CFU/mL of the working dilution used to inoculate each microtiter plate was made by preparing 6 serial dilutions of the inoculum (0.1 mL inoculum in 0.9 mL of the appropriate broth) and pipetting 20 μl of each dilution onto the appropriate agar plate to check that a proper dilution was made and that the inoculum contained $10^4$-$10^5$ CFU/mL. Agar plates were incubated at 37° C. in air plus 5% $CO_2$ until colonies were visible and could be counted. Time required until growth becomes visible varies according to species, ranging from 24-72 hours for *Ureaplasma* species and *M. hominis* up to several days for *M. pneumoniae* and *M. genitalium*. Microdilution trays were incubated aerobically at 37° C. and examined after 18-24 hours and then daily for color change in the growth control wells.

Determination of MIC Endpoints, Quality Control, and Assay Validation.

MICs were recorded as the lowest concentration of antimicrobial agent inhibiting color change in broth medium at the time when the organism control well first showed color change. A positive reaction for growth of *Ureaplasma* spp. in 10B broth was evidenced by a color change from yellow to pink in the organism control well (i.e. well 12). A positive reaction for *M. hominis* in *Mycoplasma* broth was evidenced by a color change from pink to deeper red in the organism growth control well (i.e. well 12). A positive reaction for *M. pneumoniae* and *M. genitalium* in SP4 broth was evidenced by a color change from pink to yellow in the growth control well. Results were considered valid if the control agar plate for organism's concentration indicated that there were between $10^4$ and $10^5$ CFU/mL. Control wells and expected results were: well 9 (solvent control)—no color change; well 10 (media control)—no color change; well 11 (drug control)—no color change; well 12 (growth control)—growth and color change according to which organism is being tested, without turbidity. By performing CFU quantification on the inoculum of each isolate tested, purity of the organisms was verified. SP4 agar detects contaminants or mixed cultures with *Mycoplasma* species when inoculated with *M. pneumoniae* and *M. genitalium. M. hominis* grows on either SP4 or *mycoplasma* agar. *M. hominis* and commensal respiratory *Mycoplasma* species produce fried egg colonies whereas; *M. pneumoniae* and *M. genitalium* produce small spherical colonies. A8 agar plates yield brown granular colonies for *Ureaplasma* species and would also detect contaminating *Mycoplasma* species or bacteria. Any turbidity in the growth control well indicates bacterial contamination and invalidates the results.

Broth Microdilution MIC Quality Control Limits.

For quality control (QC) purposes, American Type Culture Collection (ATCC) strains designated by the CLSI (CLSI 2011) for each organism being tested were included with each assay every day of performance. MIC reference ranges for several antimicrobial agents have been established for these strains (CLSI 2011). QC strains that were used were: *M. pneumoniae* ATCC 29342, *M. hominis* ATCC 23114, and *U. urealyticum* ATCC 33175. There is no *M. genitalium* type strain recommended by the CLSI since susceptibility testing has not been standardized for this organism. Therefore, we chose the type strain ATCC 33530 for this organism. This strain has been used in our laboratory for other investigations and has predictable MICs for several antimicrobial agents. Acceptable MIC QC limits for a single test (single-drug/single organism combination) are listed in Table 3 as derived from the CLSI document (CLSI 2011). QC strains performed as expected for all MIC assays for which data are presented.

TABLE 3

MIC Limits (μg/mL) for Quality Control Strains for *Mycoplasma hominis*, *Mycoplasma pneumoniae* and *Ureaplasma urealyticum* Tested by Broth Microdilution

| Antimicrobial Agent | *Mycoplasma hominis* ATCC 23114 | *Mycoplasma pneumoniae* ATCC 29342 | *Ureaplasma urealyticum* ATCC 33175 |
|---|---|---|---|
| Azithromycin | — | — | 0.5-8 |
| Clindamycin | 0.0032-0.25 | 0.25-4 | 2-32 |
| Erythromycin | — | 0.004-0.063 | 1-8 |
| Levofloxacin | 0.032-0.5 | 0.125-1 | 0.5-2 |
| Moxifloxacin | 0.016-0.125 | 0.032-0.25 | 0.5-2 |
| Telithromycin | — | — | 0.125-1 |
| Tetracycline | — | 0.063-1 | 16-256 |

Note for Table 3

Data in Table 3 were derived from the M-43-A CLSI Document (CLSI 2011).

Results

*M. genitalium.*

Compound 1 showed in vitro activity comparable to that of levofloxacin and doxycycline. The overall MIC range for these three drugs was within 4 2-fold dilutions=0.25-2 μg/mL. Compound 1 MIC range 0.5-1 μg/mL) was less potent than azithromycin (MIC range <0.001 μg/mL).

*M. pneumoniae.*

The $MIC_{90}$ for Compound 1 (1 μg/mL) was equivalent to that of levofloxacin and 4-fold higher than doxycycline (0.25 μg/mL). Most *M. pneumoniae* isolates had azithromycin MICs <0.001 μg/mL, but two strains were chosen for testing because they had azithromycin MICS of 16 and 32 μg/mL and contained mutations in 23S ribosomal RNA.

Compound 1 maintained in vitro potency against these two macrolide-resistant isolates comparable to that for those isolates that were fully macrolide-susceptible.

*M. hominis.*

Compound 1 had the lowest overall activity against *M. hominis* with the $MIC_{90}$ of 4 μg/mL and a maximum MIC value of 8 μg/mL. Doxycycline MICs for *M. hominis* isolates without tetM ranged from 0.016-0.063 μg/mL, while MICs for those three with tetM were 4 μg/mL. Corresponding tetracycline MICs were 32 μg/mL for those isolates. Compound 1 MICs for doxycycline not affected by the presence of tetM. $MIC_{90}$ for Compound 1 (4 μg/mL) was 16-fold greater than that of levofloxacin (0.25 μg/mL) and was equivalent to that of azithromycin, a drug that is not usually very active against this species. Without having information on achievable drug concentrations for Compound 1, it is not possible to indicate whether these MICs would be considered susceptible or resistant.

*Ureaplasma* Species.

The $MIC_{90}$ for Compound 1 was 1 μg/mL, making it comparable to levofloxacin in potency. There was no difference in Compound 1 MICs against levofloxacin-resistant ureaplasmas and levofloxacin-susceptible isolates. Similarly, among three *Ureaplasma* isolates containing tetM, MICs for Compound 1 were not affected with its MICs ranging from 0.5-2 μg/mL versus 4-8 μg/mL for doxycycline, but $MIC_{90}$ for doxycycline-susceptible organisms (0.125 μg/mL) was 8-fold more active than Compound 1 (1 μg/mL). The Compound 1 MIC for the single macrolide-resistant isolate of *U. urealyticum* (azithromycin MIC=32 μg/mL) was 2 μg/mL, which was 2-fold dilution higher than the $MIC_{90}$ for this drug, but overall, Compound 1 was 4-fold more potent than azithromycin ($MIC_{90}$ of 1 vs 4 μg/mL).

TABLE 4

MIC Dataset for Compound 1 and Three Comparators Tested Against Human Mycoplasmas

| Accession No. or stock identifier | Compound 1 | AZI | DOX | LEV |
|---|---|---|---|---|
| *Mycoplasma genitalium* (n = 5) MICs (μg/mL) | | | | |
| M2341 | 0.5 | <0.001 | 1 | 0.5 |
| M30 | 1 | <0.001 | 0.25 | 2 |
| M2321 | 0.5 | <0.001 | 1 | 0.5 |
| M6282 | 0.5 | <0.001 | 1 | 0.5 |
| UTMB-10G | 0.5 | <0.001 | 0.5 | 2 |
| G37 | 0.5 | <0.001 | 0.25 | 2 |
| QC Strain ATCC 33530 | | | | |
| *Mycoplasma pneumoniae* (n - 12) MICs (μg/mL) | | | | |
| 54484 | 0.5 | 32 | 0.25 | 0.5 |
| 54506 | 0.5 | 16 | 0.25 | 0.5 |
| 55246 | 1.0 | <0.001 | 0.25 | 1 |
| 55612 | 1.0 | <0.001 | 0.25 | 0.5 |
| 57807 | 0.5 | <0.001 | 0.25 | 0.5 |
| 58188 | 0.5 | <0.001 | 0.125 | 0.5 |
| 58772 | 0.5 | <0.001 | 0.5 | 1 |
| 59598 | 0.5 | <0.001 | 0.25 | 1 |
| 59597 | 0.5 | <0.001 | 0.25 | 0.5 |
| 53938 | 0.5 | <0.001 | 0.25 | 1 |
| 53706 | 0.5 | <0.001 | 0.25 | 0.5 |
| 51494 | 0.5 | <0.001 | 0.25 | 1 |
| M-129 | 0.5 | <0.001 | 0.5 | 1 |
| QC Strain ATCC 29342-B7 | | | | |
| *Mycoplasma hominis* (n = 12) MICs (μg/L) | | | | |
| 10848 | 8 | 8 | 4 | 0.25 |
| 10505 | 2 | 4 | 4 | 0.063 |
| 59793 | 2 | 4 | 0.032 | 0.25 |
| 59744 | 2 | 2 | 0.016 | 0.125 |
| 58881 | 4 | 4 | 0.032 | 0.25 |
| 58603 | 1 | 1 | 0.032 | 0.125 |
| 11124 | 2 | 1 | 0.032 | 0.25 |
| 11063 | 4 | 4 | 0.063 | 0.125 |
| 11140 | 4 | 1 | 4 | 0.125 |
| 11121 | 1 | 4 | 0.032 | 0.125 |
| 11612 | 4 | 4 | 0.016 | 0.25 |
| 12434 | 4 | 2 | 0.032 | 0.125 |
| PG21 | 2 | 1 | 0.032 | 0.5 |
| QC Strain ATCC 23114 | | | | |

TABLE 4-continued

| *Ureaplasma* species (n -15) MICs (μg/mL) | | | | | |
|---|---|---|---|---|---|
| Accession No. or stock identifier | Species | Compound 1 | AZI | DOX | LEV |
| 25353 | Uu | 2 | 32 | 8 | 8 |
| 48105 | Up | 0.5 | 2 | 0.125 | 32 |
| 48736 | Up | 0.5 | 1 | 0.063 | 1 |
| 51110 | Up | 0.5 | 1 | 0.016 | 8 |
| 49718 | Uu | 1 | 2 | 8 | 1 |
| 50826 | Uu | 0.5 | 2 | 4 | 0.5 |
| 43306 | Uu | 1 | 4 | 0.125 | 1 |
| 44062 | Uu | 1 | 4 | 0.25 | 1 |
| 45623 | Up | 0.25 | 1 | 0.016 | 0.25 |
| 48750 | Up | 0.125 | 1 | 2 | 0.25 |
| 52863 | Up | 0.5 | 2 | 0.125 | 1 |
| 59913 | Up/Uu | 0.5 | 2 | 0.125 | 1 |
| 59967 | Up | 0.5 | 4 | 0.063 | 1 |
| 60052 | Up/Uu | 0.5 | 2 | 0.125 | 1 |
| 60153 | Up/Uu | 0.5 | 2 | 0.063 | 4 |
| Uu Serotype 9 | Uu | 0.5 | 2 | 8 | 1 |
| QC Strain ATCC 33175 | | | | | |

TABLE 5

Data Summary for Compound 1 and Three Comparators Tested Against Human Mycoplasmas

| | Compound 1 | Azithromycin | Doxycycline | Levofloxacin |
|---|---|---|---|---|
| *M. genitalium* MICs (μg/mL) n = 5 | | | | |
| Range | 0.5-1 | <0.001 | 0.25-1 | 0.5-2 |
| M2341 | 0.5 | <0.001 | 1 | 0.5 |
| M30 | 1 | <0.001 | 0.25 | 2 |
| M2321 | 0.5 | <0.001 | 1 | 0.5 |
| M6282 | 0.5 | <0.001 | 1 | 0.5 |
| UTMB | 0.5 | <0.001 | 0.5 | 2 |

TABLE 5-continued

Data Summary for Compound 1 and Three Comparators Tested Against Human Mycoplasmas

| | Compound 1 | Azithromycin | Doxycycline | Levofloxacin |
|---|---|---|---|---|
| G37 QC Strain ATCC 33530 | 0.5 | <0.001 | 0.25 | 2 |
| *M. pneumoniae* MICs (μg/mL) n = 12 | | | | |
| Range | 0.5-1 | <0.001-32 | 0.125-0.5 | 0.5-1 |
| $MIC_{50}$ | 0.5 | <0.001 | 0.25 | 0.5 |
| $MIC_{90}$ | 1 | 16 | 0.25 | 1 |
| M-129-B7 QC Strain ATCC 29342 | 0.5 | <0.001 | 0.5 | 1 |
| *M. hominis* MICs (μg/mL) n = 12 | | | | |
| Range | 1-8 | 1-8 | 0.016-4 | 0.063-0.25 |
| $MIC_{50}$ | 2 | 4 | 0.032 | 0.125 |
| $MIC_{90}$ | 4 | 4 | 4 | 0.25 |
| PG21 QC Strain ATCC 23114 | 2 | 1 | 0.032 | 0.5 |
| *Ureaplasma* species (μg/mL) n = 15 | | | | |
| Range | 0.125-2 | 1-32 | 0.016-8 | 0.25-32 |
| $MIC_{50}$ | 0.5 | 2 | 0.125 | 1 |
| $MIC_{90}$ | 1 | 4 | 8 | 8 |
| Uu Serotype 9 QC Strain ATCC 33175 | 0.5 | 2 | 8 | 1 |

Notes for Tables 4 and 5

Abbreviations

AZI=azithromycin, DOX=doxycycline, LEV=levofloxacin, Uu=*Ureaplasma urealyticum*, Up=*Ureaplasma parvum.*

The 3 *M. hominis* isolates containing the tetM gene were also tested against tetracycline at the same time as doxycycline. All 3 isolates had MICs of 32 μg/mL for tetracycline.

DISCUSSION

*Mycoplasma* and *Ureaplasma* species that infect humans can cause significant disease in the respiratory tracts as well as the urogenital tracts. In addition to *N. gonorrhoeae* and *Chlamydia trachomatis*, both *M. genitalium* and *Ureaplasma urealyticum* can cause male urethritis and *M. genitalium* also causes female cervicitis and pelvic inflammatory disease (Waites K B, Taylor-Robinson D. *Mycoplasma* and *Ureaplasma*. Manual of Clinical Microbiology, 10th Ed. Washington, D.C., ASM Press: 970-985, 2011). Invasive infections of the bloodstream, CSF, and lungs sometimes occur due to *M. hominis* and *Ureaplasma* species in neonates (Waites and Taylor-Robinson 2011). Invasive disease may also occur in adults in the setting of immunodeficiency (Waites and Taylor-Robinson 2011).

Treatment options for mycoplasmal and ureaplasmal infections are no longer clear-cut since macrolide resistance is becoming very common in *M. pneumoniae* in Asia and is spreading gradually to Europe and North America; tetracyline resistance rates may approach 50% in *M. hominis* and *Ureaplasma* species in some areas; and resistance to macrolides and fluoroquinolones has been well documented among the genital mycoplasmas (Waites K B, Lysynyansky I, Bebear C M. (2014). Emerging antimicrobial resistance in mycoplasmas of humans and animals. Mollicutes Molecular Biology and Pathogenesis. G. Browning and C. Citti. Norfolk, UK, Caister Academic Press: 289-322). Patients who are immunosuppressed and those who have received numerous courses of antibiotics over time are at greater risk for having infections with drug-resistant organisms (Waites 2014). For these reasons, new agents that are not affected by cross-resistance to other drug classes such as macrolides, tetracyclines, and fluoroquinolones are needed.

This small preliminary study has demonstrated that Compound 1 has in vitro activity against *M. genitalium, M. pneumoniae, U. urealyticum* and *U. parvum* that is comparable to levofloxacin, another agent targeting DNA replication, and its potency was unaffected by presence of mutations conferring fluoroquinolone resistance. Furthermore, resistance to macrolides and tetracyclines in *Mycoplasma* and *Ureaplasma* species appeared not to have any significant measurable effect on MICs of Compound 1, though more isolates should be tested to confirm this observation. Azithromycin was the most potent agent tested against *M. genitalium* and *M. pneumoniae* in the absence of mutations that affect macrolide binding to the ribosomes. The $MIC_{90}$ for Compound 1 was 4-fold less than azithromycin against *Ureaplasma* species, making it the most active drug among the four agents tested.

CONCLUSIONS

- Compound 1 activity in vitro against *M. pneumoniae, M. genitalium* and *Ureaplasma* species was similar overall to levofloxacin with all MICs <2 μg/mL, while its potency against *M. hominis* was somewhat less in terms of $MIC_{90}$ (4 μg/mL).
- The $MIC_{90}$ (1 μg/mL) of Compound 1 was 4-fold lower than that of azithromycin against *Ureaplasma* species, making it the most potent of the four agents tested against these organisms.
- The activity of Compound 1 in vitro against *M. pneumoniae, M. hominis* and *Ureaplasma* species was not affected by mutations conferring macrolide or fluoroquinolone resistance, or by the presence of tetM in the small number of isolates tested.

Compound 1 may be a potentially useful agent for further development as a possible treatment for infections caused by human mycoplasmas and ureaplasmas in the urogenital tract or respiratory tract.

Example 3. In Vitro Antibacterial Activity of Compound 1 Against Potential Agents of Bioterrorism The potential of Category A and B Select Agents for use as agents of bioterrorism is well documented. To this end, we established antimicrobial susceptibility profiles for compounds from multiple drug classes and for Compound 1 against multiple isolates each of *Bacillus anthracis* (*B. anthracis*), *Burkholderia mallei* (*B. mallei*), *Burkholderia pseudomallei* (*B. pseudomallei*), *Brucella abortus* (*B. abortus*), *Brucella melitensis* (*B. melitensis*), *Brucella suis* (*B. suis*), *Francisella tularensis* (*F. tularensis*) and *Yersina pestis* (*Y. pestis*). Testing was conducted in a broth microdilution assay format following Clinical and Laboratory Standards Institute (CLSI) guidelines. Results were reported as the lowest concentration (μg/mL) of antimicrobial agent that completely inhibited growth of the organism in the microdilution wells visually.

Materials and Methods

Antibacterials

Three (3) comparator compounds (doxycycline, levofloxacin and chloramphenicol) and Compound 1 were screened for antibacterial activity against multiple isolates each of *Bacillus anthracis* (*B. anthracis*), *Burkholderia mallei* (*B. mallei*), *Burkholderia pseudomallei* (*B. pseudomallei*), *Brucella abortus* (*B. abortus*), *Brucella melitensis* (*B. melitensis*), *Brucella suis* (*B. suis*), *Francisella tularensis* (*F. tularensis*) and *Yersina pestis* (*Y. pestis*). Compounds were prepared according to instructions provided by the Sponsor and in accordance with CLSI guidelines. A total of 12 concentrations each for all test and comparator compounds were tested in triplicate. The concentration range was a two-fold dilution scheme with a starting concentration of 64 μg/mL and an ending concentration of 0.031 μg/mL.

Bacterial Strains

Ten isolates each of *B. anthracis, Y. pestis, B. mallei, B. pseudomallei, B. suis, B. melitensis, B. abortus* and 3 isolates of *F. tularensis* were utilized for drug screening (Table 6). In addition, the following quality control strains were included: *E. coli* 25922, *S. aureus* 29213, *P. aeruginosa* 27853, *S. pneumoniae* 49619 and *E. coli* 35218.

TABLE 6

| Bacterial Isolates Screened | | |
|---|---|---|
| *Bacillus anthracis* | Ames | [1]Health Protection Agency |
| | 36 | Culture Collections; Porton |
| | 38 | Down, UK |
| | 41 | [2]BEI Resources; Manassas, |
| | 46 | VA |
| | 411 | |
| | 412 | |
| | 413 | |
| | 415 | |
| *Burkholderia mallei* | 120 | [1]Health Protection Agency |
| | 3708 | Culture Collections; Porton |
| | 3709 | Down, UK |
| | 10229 | [2]BEI Resources; Manassas, |
| | 10230 | VA |
| | 10245 | |
| | 10247 | |

TABLE 6-continued

| Bacterial Isolates Screened | | |
|---|---|---|
| | 10248 | |
| | 10260 | |
| | 12938 | |
| *Burkholderia pseudomallei* | 1688 | [1]Health Protection Agency |
| | 4845 | Culture Collections; Porton |
| | 4846 | Down, UK |
| | 6700 | [2]BEI Resources; Manassas, |
| | 7383 | VA |
| | 7431 | |
| | 8016 | |
| | 8707 | |
| | 8708 | |
| | 10274 | |
| *Brucella abortus* | 624 | [1]Health Protection Agency |
| | 1408 | Culture Collections; Porton |
| | 3605 | Down, UK |
| | 4487 | [2]BEI Resources; Manassas, |
| | 5059 | VA |
| | 7470 | |
| | 7471 | |
| | 7472 | |
| | 8038 | |
| | 8200 | |
| | 3511 | |
| | 3605 | |
| | 8200 | |
| *Brucella melitensis* | 8223 | [1]Health Protection Agency |
| | 8334 | Culture Collections; Porton |
| | 8631 | Down, UK |
| | 8632 | [2]BEI Resources; Manassas, |
| | 10200 | VA |
| | 10502 | |
| | 11361 | |
| *Brucella suis* | 3142 | [1]Health Protection Agency |
| | 3143 | Culture Collections; Porton |
| | 4490 | Down, UK |
| | 5061 | [2]BEI Resources; Manassas, |
| | 10095 | VA |
| | 10098 | |
| | 10385 | |
| | 10510 | |
| | 10511 | |
| | 10364 | |
| *Francisella tularensis* | 643 | [1]Health Protection Agency |
| | 644 | Culture Collections; Porton |
| | 645 | Down, UK |
| | | [2]BEI Resources; Manassas, |
| | | VA |
| *Yersinia Pestis* | CO92 | [1]Health Protection Agency |
| | 16 | Culture Collections; Porton |
| | 17 | Down, UK |
| | 20 | [2]BEI Resources; Manassas, |
| | 637 | VA |
| | 639 | [3]Lovelace Respiratory |
| | 640 | Research Institute; |
| | 8775 | Albuquerque, NM |
| | 10029 | |
| | 10030 | |

In Vitro Susceptibility Test Methods (as Appropriate)

Testing was conducted utilizing the broth microdilution methodology outlined by CLSI guidelines. Briefly, testing was conducted using 96-well, U-bottom microplates with an assay volume of 0.2 mL/well. Plates containing appropriate broth and two-fold dilutions of the test compounds were inoculated with a targeted concentration of 5.0×105 CFU/mL (5.0×104 CFU/well) of bacterial agent and subsequently incubated for 24-72 hours depending on the agent. Following incubation, the plates were read visually and individual wells scored for turbidity, partial clearing or complete clearing. The MIC was reported as the lowest concentration (μg/mL) of drug that visually inhibited growth of the organism. Growth medium, inoculum preparation and incubation conditions are provided below in Table 7.

TABLE 7

| Growth Medium, Inoculum Preparation and Incubation Conditions | | | |
|---|---|---|---|
| Organism | Medium | Inoculum | Incubation |
| *Bacillus anthracis* | CAMHB | Direct Colony Suspension | 37° C., ~18 hours |
| *Brucella abortus* | *Brucella* Broth pH 7.1 ± 0.1 | Growth Method | 37° C., 48 hours |
| *Brucella melitensis* | *Brucella* Broth pH 7.1 ± 0.1 | Growth Method | 37° C., 48 hours |
| *Brucella suis* | *Brucella* Broth pH 7.1 ± 0.1 | Growth Method | 37° C., 48 hours |
| *Burkholderia mallei* | CAMHB | Growth Method | 37° C., ~18 hours |
| *Burkholderia pseudomallei* | CAMHB | Growth Method | 37° C., ~18 hours |
| *Francisella tularensis* | CAMHB + 2% IsoVitaleX ™ | Direct Colony Suspension | 37° C., 48-72 hours |
| *Yersinia pestis* | CAMHB | Growth Method | 28° C., 24-48 hours |

The results of the screen described above are shown in Table 8 and 9.

TABLE 8

| Antimicrobial Susceptibility of Compound 1 and Three Comparators Against Select Bacteria | | | | |
|---|---|---|---|---|
| Organism | Compound 1 MIC (μg/mL) | Doxycycline MIC (μg/mL) | Chloram-phenicol MIC (μg/mL) | Levofloxacin MIC (μg/mL) |
| *Burkholderia pseudomallei* | 32 | 0.5 | 16 | 4 |
| | 32 | 0.5 | 8 | 2 |
| | 32 | 0.5 | 8 | 2 |
| | 64 | 0.5 | 16 | 4 |
| | 32 | 0.063 | 4 | 4 |
| | 32 | 0.5 | 16 | 4 |
| | 32 | 8 | >256 | 16 |
| | 32 | 0.25 | 8 | 8 |
| | 64 | 0.25 | 8 | 4 |
| | 32 | 8 | 64 | 8 |
| *Burkholderia mallei* | 4 | ≤0.031 | 4 | 0.5 |
| | 0.25 | ≤0.031 | 1 | ≤0.125 |
| | 4 | ≤0.031 | 4 | 0.25 |
| | 64 | ≤0.031 | 1 | 0.5 |
| | 32 | 0.063 | 8 | 0.5 |
| | 2 | ≤0.031 | 8 | ≤0.125 |
| | 8 | ≤0.031 | 4 | ≤0.125 |
| | 0.5 | ≤0.031 | 1 | ≤0.125 |
| | 2 | ≤0.031 | 4 | 0.5 |
| | 2 | 0.063 | 4 | 0.25 |
| *Brucella abortus* | 8 | 0.25 | 1 | 0.5 |
| | 4 | 0.25 | 1 | 0.25 |
| | 8 | 0.125 | 1 | 0.25 |
| | 4 | 0.125 | 2 | 0.25 |
| | 4 | 0.25 | 2 | 0.25 |
| | 0.063 | 0.063 | 0.5 | 0.25 |
| | 1 | 0.25 | 2 | 0.25 |
| | 0.5 | 0.063 | 1 | 0.25 |
| | 1 | 0.063 | 2 | 0.25 |
| | 16 | 0.5 | 4 | 0.5 |
| *Yersinia pestis* | 2 | 0.5 | 4 | ≤0.25 |
| | 2 | 0.5 | 8 | ≤0.25 |
| | 2 | 0.5 | 8 | ≤0.25 |
| | >64 | 1 | 8 | 0.25 |
| | 2 | 1 | 4 | ≤0.25 |
| | 2 | 1 | 2 | ≤0.25 |
| | 2 | 0.5 | 8 | ≤0.25 |
| | 1 | 0.5 | 8 | 0.25 |
| | 2 | 0.5 | 8 | ≤0.25 |
| | 2 | 1 | 8 | ≤0.25 |
| *Francisella tularensis* | 16 | 4 | 2 | ≤0.125 |
| | 8 | 1 | 2 | ≤0.125 |
| | 16 | 2 | 1 | ≤0.125 |

TABLE 8-continued

| Antimicrobial Susceptibility of Compound 1 and Three Comparators Against Select Bacteria | | | | |
|---|---|---|---|---|
| Organism | Compound 1 MIC (μg/mL) | Doxycycline MIC (μg/mL) | Chloram-phenicol MIC (μg/mL) | Levofloxacin MIC (μg/mL) |
| *Bacillus anthracis* | 0.5 | ≤0.031 | 8 | ≤0.25 |
| | 0.125 | ≤0.031 | 8 | ≤0.25 |
| | 0.125 | ≤0.031 | 4 | ≤0.25 |
| | 0.25 | ≤0.031 | 8 | ≤0.25 |
| | 0.5 | ≤0.031 | 4 | ≤0.25 |
| | 0.125 | ≤0.031 | 8 | ≤0.25 |
| | 1 | ≤0.031 | 8 | ≤0.25 |
| | 0.5 | ≤0.031 | 8 | ≤0.25 |
| | 0.05 | ≤0.031 | 8 | ≤0.25 |
| | 0.125 | ≤0.031 | 8 | ≤0.25 |
| *Brucella melitensis* | 8 | 0.25 | 4 | 0.5 |
| | 8 | 0.125 | 2 | 0.5 |
| | 16 | 0.25 | 8 | 1 |
| | 8 | 0.25 | 4 | 0.25 |
| | 8 | 0.125 | 4 | 0.5 |
| | 8 | 0.125 | 4 | 0.5 |
| | 8 | 0.125 | 4 | 0.5 |
| | 8 | 0.125 | 2 | 0.25 |
| | 8 | 0.125 | 4 | 0.5 |
| | 16 | 0.125 | 4 | 0.5 |
| *Brucella suis* | 2 | 0.063 | 2 | 0.5 |
| | 1 | 0.063 | 1 | 0.25 |
| | 1 | 0.063 | 1 | 0.5 |
| | 1 | 0.125 | 2 | 0.5 |
| | 1 | 0.063 | 2 | 0.5 |
| | 2 | 0.125 | 2 | 0.25 |
| | 1 | 0.063 | 4 | 0.5 |
| | 1 | 0.063 | 2 | 0.5 |
| | 1 | 0.063 | 1 | 0.25 |
| | 1 | 0.063 | 2 | 0.5 |

TABLE 9

| In vitro activity of Compound 1 (ug/ml) | | | | |
|---|---|---|---|---|
| Organism | N | Range | $MIC_{50}$ | $MIC_{90}$ |
| *Bacillus anthracis* | 10 | 0.12-1 | 0.25 | 0.5 |
| *B. anthracis* | 30 | 0.12-4 | 0.25 | 1 |
| *Brucella suis* | 10 | 1-2 | 1 | 2 |
| *Burkholderia mallei* | 10 | 0.25-64 | 2 | 32 |
| *B. mallei* | 30 | 2-32 | 16 | 32 |
| *Burkholderia pseudomallei* | 10 | 32-64 | 32 | 64 |
| *B. pseudomallei* | 28 | 32->32 | 32 | >64 |
| *Francisella tularensis* | 27 | 8-16 | 16 | 16 |
| *Yersinia pestis* | 10 | 1->64 | 2 | 2 |
| *Y. pestis* | 30 | 2-8 | 4 | 8 |

The invention claimed is:

1. A method for treating a bacterial infection caused by one or more bacterium selected from *Bacillus anthracis, Bacillus cereus, Burkholderia* spp., *Brucella* spp., *Francisella* spp., *Yersinia* spp., *Mycoplasma* spp., *Ureaplasma* spp., *Chlamydia trachomatis* and *Chlamydia pneumoniae* in a subject in need thereof comprising administering an effective amount of (2R,4S,4aS)-11-fluoro-2,4-dimethyl-8-[(4S)-4-methyl-2-oxo-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione, or a pharmaceutically acceptable salt thereof, to the subject.

2. The method of claim 1, wherein the subject is a human.

3. The method of claim 1, wherein the subject is suffering from more than one bacterial infection.

4. The method of claim 3, wherein the subject is suffering from a *Chlamydia trachomatis* infection and a *Neisseria gonorrhoeae* infection.

5. The method of claim 1, wherein the bacteria is resistant to one or more antibacterials other than (2R,4S,4aS)-11-fluoro-2,4-dimethyl-8-[(4S)-4-methyl-2-oxo-1,3-oxazolidin-3-yl]-1,2,4,4a-tetrahydro-2'H,6H-spiro[1,4-oxazino[4,3-a][1,2]oxazolo[4,5-g]quinoline-5,5'-pyrimidine]-2',4',6'(1'H,3'H)-trione.

6. The method of claim 1, wherein the bacterial infection caused by one or more bacteria selected from *Bacillus anthracis, Brucella* spp., *Francisella* spp., *Yersinia* spp., *Mycoplasma* spp., *Ureaplasma* spp., *Chlamydia trachomatis* and *Chlamydia pneumoniae.*

* * * * *